US012415025B2

(12) United States Patent
Denison et al.

(10) Patent No.: US 12,415,025 B2
(45) Date of Patent: Sep. 16, 2025

(54) PHYSIOLOGIC CARDIOVASCULAR PH BALANCED COUNTER CURRENT ELECTROLYTE TRANSFER AND FLUID REMOVAL SYSTEM

(71) Applicants: Richard Denison, Austin, TX (US); Mary Claire McGarry, Houston, TX (US)

(72) Inventors: Richard Denison, Austin, TX (US); Mary Claire McGarry, Houston, TX (US)

(73) Assignee: NEPHRATECH LLC, Austin, TX (US)

( * ) Notice: Subject to any disclaimer, the term of this patent is extended or adjusted under 35 U.S.C. 154(b) by 953 days.

(21) Appl. No.: 17/048,855

(22) PCT Filed: Apr. 18, 2019

(86) PCT No.: PCT/US2019/028101
§ 371 (c)(1),
(2) Date: Oct. 19, 2020

(87) PCT Pub. No.: WO2019/204589
PCT Pub. Date: Oct. 24, 2019

(65) Prior Publication Data
US 2021/0236710 A1 Aug. 5, 2021

Related U.S. Application Data

(60) Provisional application No. 62/659,951, filed on Apr. 19, 2018.

(51) Int. Cl.
*A61M 1/36* (2006.01)
*A61M 1/16* (2006.01)
*A61M 1/34* (2006.01)

(52) U.S. Cl.
CPC ........ *A61M 1/3666* (2013.01); *A61M 1/1698* (2013.01); *A61M 1/3403* (2014.02);
(Continued)

(58) Field of Classification Search
CPC .............. A61M 1/3609; A61M 1/3645; A61M 1/3666; A61M 1/1698; A61M 1/3403; A61M 1/3623; A61M 2230/208
See application file for complete search history.

(56) References Cited

U.S. PATENT DOCUMENTS 5,308,320 A * 5/1994 Safar ..................... A61M 60/38
604/113
6,689,083 B1 * 2/2004 Gelfand ................ A61M 1/367
210/741
(Continued)

FOREIGN PATENT DOCUMENTS

WO WO 2016/205221 12/2016

OTHER PUBLICATIONS

International Preliminary Report on Patentability Issued in Corresponding PCT Patent Application No. PCT/US2019/028101, dated Oct. 20, 2020.
(Continued)

*Primary Examiner* — Guy K Townsend
*Assistant Examiner* — Peter Daniel Smith
(74) *Attorney, Agent, or Firm* — Panitch Schwarze Belisario & Nadel LLP (57) ABSTRACT

Certain embodiments of the invention are directed to methods of adjusting the concentration of one or more electrolytes in a patient's blood using a counter current electrolyte solution.

32 Claims, 2 Drawing Sheets

(52) U.S. Cl.
CPC ......... *A61M 1/3609* (2014.02); *A61M 1/3623* (2022.05); *A61M 2230/208* (2013.01)

(56) References Cited

U.S. PATENT DOCUMENTS

| | | | |
|---|---|---|---|
| 2005/0197612 A1* | 9/2005 | Levin .................. | A61M 1/3639 604/6.11 |
| 2011/0237996 A1 | 9/2011 | Kotanko et al. | |
| 2012/0018377 A1 | 1/2012 | Tsukamoto | |
| 2014/0158623 A1 | 6/2014 | Pudil et al. | |
| 2015/0335807 A1 | 11/2015 | Kellum | |
| 2016/0067278 A1 | 3/2016 | Bryland et al. | |
| 2017/0000938 A1* | 1/2017 | Wilt .................... | F04B 43/0054 |
| 2017/0209634 A1 | 7/2017 | Maierhofer | |
| 2017/0304516 A1* | 10/2017 | Burnes ................ | A61M 1/1601 |
| 2020/0230309 A1* | 7/2020 | Treu .................... | A61M 1/3623 |

OTHER PUBLICATIONS

International Search Report and Written Opinion Issued in Corresponding PCT Patent Application No. PCT/US2019/028101, mailed Jul. 10, 2019.

Pittard, et al., "Chapter 13—Safety Monitors in Hemodialysis," Handbook of Dialysis Therapy (5$^{th}$ Edition): 162-190.e2, 2017.

* cited by examiner

PHYSIOLOGIC CARDIOVASCULAR PH BALANCED COUNTER CURRENT ELECTROLYTE TRANSFER AND FLUID REMOVAL SYSTEM

CROSS REFERENCE TO RELATED APPLICATIONS

This application is a national phase application under 35 U.S.C. § 371 of International Application No. PCT/US2019/028101, filed Apr. 18, 2019, which claims the benefit of priority to U.S. Provisional Patent Application Ser. No. 62/659,951, filed Apr. 19, 2018, hereby incorporated by reference in its entirety.

BACKGROUND OF THE INVENTION

A. Field of the Invention

The invention generally concerns a system or device for adjusting the concentration of at least one electrolyte in a fluid, such as blood, and methods related to the same.

B. Description of Related Art

In order for the cardiac surgeon to repair cardiac defects, the majority of the operations require the use of cardiopulmonary bypass. Cardiopulmonary bypass includes a heart/lung machine, with various pumps, an artificial lung or oxygenator, a heater/cooler for temperature control and an artificial kidney or hemofilter. None of these features of cardiopulmonary bypass is actually physiological in comparison to the patient's physiological process under normal circumstances. However, the clinical practitioners or perfusionist is in charge of monitoring and maintaining physiological conditions of the patient's circulation, ventilation, oxygenation, anticoagulation, fluid and electrolyte balance throughout the entire bypass surgery. Although, there have been vast improvements in the heart/lung machine, as well as the disposables over the past half century, the process of fluid and electrolyte balance has not changed much, if at all.

The accepted crystalloid fluids, 0.9% NaCl and Plasmalyte, which are used during cardiopulmonary bypass have been unchanged for the last few decades. If these crystalloids are examined closely, it is found that these solutions have a low pH and the sodium and chloride concentration (0.9% NaCl) are not physiological. But, the industry wide accepted practice to attempt to manipulate the electrolytes begins with the perfusionist selecting a crystalloid solution that lacks the electrolyte value they are trying to change. For instance, if a patient's elevated potassium level is to be reduced, the perfusionist will most likely select 0.9% NaCl as their crystalloid, which is potassium free. The process begins by adding 0.9% NaCl into the patient's bypass circuit reservoir then removing it via a hemofilter. By adding this potassium free solution into the circuit and filtering with ultrafiltration, the potassium level in the patient's blood will eventually be reduced. This accepted process is inefficient, as well as leaving the patient's blood in a more acidotic state. To bring the pH back into a physiological range, it is necessary to treat the induced acidosis by administering sodium bicarbonate, which in turn causes the sodium level of the patient's blood to become elevated outside of the normal sodium physiological range. As can be seen, to remedy one electrolyte, another electrolyte becomes out of range. Even in routine cases, many liters of a crystalloid may be added to the patient's bypass circuit to "wash" the ultrafiltration filtrate in an attempt to maintain the patient in as close to a physiological state as possible. This antiquated, yet singular option for restoring the electrolytes, causes a host of other imbalances. The patient can all but be guaranteed metabolic acidosis, hypocalcemia, hyperchloremia, and/or hypernatremia.

There is a need for additional devices, systems, and methods for restoring or maintaining electrolyte balance of blood during medical procedures.

SUMMARY OF THE INVENTION

The traditional method of achieving electrolyte balance while on cardiopulmonary bypass is slow, inefficient, unreliable and has not changed for decades. The device, system, and/or methods described herein can be employed during cardiopulmonary bypass to reduce or balance electrolytes in a quick and safe manner. The conventional hemofilter is modified to facilitate the transfer of electrolytes, as well as facilitating fluid removal from the circuit. The pH balanced electrolyte solutions are customized to maintain the physiological conditions of the patients, for example, during heart surgery.

Embodiments of devices or systems described herein can be incorporated into or used with a cardiopulmonary bypass machine so that electrolyte balance can be regulated in a faster and more efficient manner, providing a solution to the electrolyte and pH problems associated with current methods that use crystalloids. In particular, the device and methods described herein safely and quickly change electrolytes within the bypass/patient circulation.

In certain embodiments the devices, systems, or methods described herein is capable of restoring banked blood, regardless of its age or decomposition. By way of example, the inventors have designed a system and related process to quickly and efficient maintain electrolyte balance and pH of blood, as well as restore such in non-circulating blood, which results in a more physiologically acceptable blood product having appropriate electrolyte balance and pH.

The features of the devices and methods described herein allow for the safe transfer of electrolytes during counter current flow. Dual pumps can be controlled together or individually depending on mode selection. The term "mode" is used to designate an operating process that produces a desired result. Modes include, but are not limited to (1) "zero balanced" electrolyte transfer mode, (2) fluid removal mode, (3) a combination of both electrolyte transfer and fluid removal mode, and (4) physiological restoration mode. The various modes provide a user with the appropriate functionality to maintain blood or a patient at or about a physiologic condition. The banked blood mode allows for the restoration of banked blood to an approximate normal physiologic state. Devices described herein can be portable. The portability of the device allows its use in a variety of locations, such as areas of a medical facility, e.g., operating rooms (OR), intensive care units (ICU), emergency rooms (ER) or blood banks.

Certain embodiments of the invention are directed to methods of adjusting the concentration of one or more electrolytes in a patient's blood, the method comprising: (a) providing an extracorporeal blood circuit comprising the following components in fluid communication with a patient's circulatory system: blood flow tubing, an oxygenator, a blood pump, and a hemofilter, wherein the hemofilter comprises a first filter chamber and a second filter chamber separated by a semi-permeable barrier; (b) flowing the patient's blood through the first filter chamber; (c) adjusting the concentration of at least one electrolyte in the patient's blood by flowing a first wash solution through the second filter chamber in a direction of flow opposite to the direction which the patient's blood is flowing through the first filter chamber. In certain aspects the at least one electrolyte in the patient's blood comprises at least one of hydrogen ion, sodium, potassium, calcium, chloride, glucose, bicarbonate, and lactate. In certain aspects at least one electrolyte is hydrogen ions and 1, 2, 3, 4, 5, 6, or 7 of sodium, potassium, calcium, chloride, glucose, bicarbonate, and lactate. In certain aspects at least one electrolyte is sodium and 1, 2, 3, 4, 5, 6, or 7 of hydrogen ions, potassium, calcium, chloride, glucose, bicarbonate, and lactate. In a further aspect at least one electrolyte is potassium and 1, 2, 3, 4, 5, 6, or 7 of hydrogen ions, sodium, calcium, chloride, glucose, bicarbonate, and lactate. In a further aspect at least one electrolyte is calcium and 1, 2, 3, 4, 5, 6, or 7 of hydrogen ions, sodium, potassium, chloride, glucose, bicarbonate, and lactate. In a further aspect at least one electrolyte is chloride and 1, 2, 3, 4, 5, 6, or 7 of hydrogen ions, sodium, potassium, calcium, glucose, bicarbonate, and lactate. In still a further aspect at least one electrolyte is glucose and 1, 2, 3, 4, 5, 6, or 7 of hydrogen ions, sodium, potassium, calcium, chloride, bicarbonate, and lactate. In a certain aspect at least one electrolyte is bicarbonate and 1, 2, 3, 4, 5, 6, or 7 of hydrogen ions, sodium, potassium, calcium, chloride, glucose, and lactate. In a certain aspect at least one electrolyte is lactate and 1, 2, 3, 4, 5, 6, or 7 of hydrogen ions, sodium, potassium, calcium, chloride, glucose, and bicarbonate. Step (c) can be performed for a time sufficient to cause the concentration of the at least one electrolyte in the patient's blood to adjust from a concentration outside a desired range to a concentration within the desired range. In certain aspects the desired range for hydrogen ion is pH 7.35 to 7.45, the desired range for sodium is 135 to 145 mM, the desired range for potassium is 3.5 to 4.5 mM, the desired range for calcium is 0.8 to 1.2 mM, the desired range for chloride is 95 to 115 mM, the desired range for glucose is 80 to 120 mg/dL, the desired range for bicarbonate is 22 to 28 mM, and the desired range for lactate is 0 to 2 mM. When performing step (c) the concentration of the at least one electrolyte is adjusted to a concentration within the desired range within 4, 6, 8, 10, 15, 20 minutes, including all values there between (e.g., 4, 6, 8 to 10, 15, 20 minutes), of initiating flow of the first wash solution through the second filter chamber. In a particular aspect the concentration of the at least one electrolyte is adjusted to a concentration within the desired range within 6 minutes of initiating flow of the first wash solution through the second filter chamber. In certain aspects performance of step (c) causes the concentration of the at least one electrolyte to adjust by at least 5, 10, 15, 20, 25, 30%, including all values there between (e.g., 5, 10, 15 to 20, 25, 30%, 5 to 15%, 10 to 15%, 10 to 20%, 15 to 30%), within 3 minutes. In particular aspects the concentration of the at least one electrolyte to adjust is changed by at least 15% within 3 minutes.

In certain embodiments the concentration of an electrolyte in the wash solution can be adjusted to effect a desired change in the electrolyte in the blood, e.g., if a blood electrolyte is elevated the wash solution can have a lower concentration of that electrolyte relative to the blood, alternatively if the blood electrolyte is low the was solution can have a higher concentration of that electrolyte relative to the blood. In certain aspects the first wash solution either does not comprise the at least one electrolyte (a target electrolyte) or comprises the at least one electrolyte at a concentration below the concentration of the at least one electrolyte in the blood before step (c) is performed. In a further aspect, the first wash solution comprises the at least one electrolyte at a concentration above the concentration of the at least one electrolyte in the blood before step (c) is performed. In a particular embodiments the first wash solution can have a pH of 7.35 to 7.45 and comprises 135-145 mmol/L of sodium, 22-28 mmol/L bicarbonate, 80-100 mmol/L glucose, 0.8-1.0 mmol/L calcium, 0 mmol/L potassium in one wash solution and 3.5 mmol/L potassium in another. In certain aspects the volume of the first wash solution flowed through the second filter chamber in step (c) is less than 200, 300, 400, 500, 600, 700, 800, 900, or 1000 mL, including all values there between, e.g., 200 to 1000 mL, 500 to 700 mL. In a particular aspect the volume of the first wash solution flowed through the second filter chamber in step (c) is less than 600 mL. The rate of flow of the first wash solution through the second filter chamber can be from 20, 30, 40, 50 to 60, 70, 80, 90 100 ml/min, including all values and ranges there between. The rate of flow of the patient's blood through the first filter chamber can be from 20, 30, 40, 50, 60, 70, 80, 90, 100 to 120, 140, 160, 180, 200 ml/min, including any value and range there between.

The method can further comprise stopping the flow of wash solution through the second filter chamber when the concentration of the at least one electrolyte in the patient's blood is within a desired range. In certain aspects the method can further comprise flowing a second wash solution through the second filter chamber after the concentration of the at least one electrolyte in the patient's blood is adjusted to be within a desired range, wherein the second wash solution comprises the at least one electrolyte at a concentration within the desired range.

The method can further comprise monitoring the concentration of the at least one electrolyte in the patient's blood. In certain aspects the concentration of sodium in the patient's blood remains below 140 mM or does not increase by more than 5% while the method is being performed. In a further aspect, performance of the method does not cause a decrease in the hematocrit of the patient's blood of more than 1, 2, 3, 4, 5, to 6%, including all values there between, e.g., 1 to 6%, 2 to 4%, etc. In particular aspects, performance of the method does not cause a decrease in the hematocrit of the patient's blood of more than 3%.

In certain aspects, step (c) further comprises: (i) flowing the wash solution from a wash solution reservoir through wash solution tubing coupled to a wash solution inlet port, the wash solution inlet port being in fluid communication with the second filter chamber; and (ii) flowing wash solution effluent from an effluent outlet port in fluid communication with the second filter chamber and through effluent tubing coupled to the effluent output port.

In certain embodiments the blood flow tubing is coupled to a blood input port and a blood outlet port, the blood input port and the blood output port being in fluid communication with the first filter chamber. An extracorporeal blood circuit can be coupled to a heat exchange unit. In certain aspects the extracorporeal blood circuit is comprised in a cardiopulmonary bypass system. In a further aspect the extracorporeal blood circuit is comprised in an extracorporeal membrane oxygenation system. In certain embodiments the patient is undergoing cardiac surgery. The patient can be of any age. In certain aspects the patient is 1 to 12 months old, 1, 10, 20, 30, 40 to 50, 60, 70, 80, 90 years old, including all ages there between.

In certain aspects the concentration of the at least one electrolyte is adjusted without adding fluid to a reservoir of the patient's blood. In a further aspect the concentration of the at least one electrolyte is adjusted without a transient or permanent net influx of fluid into the patient's blood. Traditional ultrafiltration methods add the wash solution into the patient circuit reservoir making direct contact with the patient's blood circulation. In certain aspects of the current method, the wash solution comes in contact with a counter current semipermeable membrane inside the hemoconcentrator, pulling fluid across the membrane, providing a more efficient method. In still a further aspect the concentration of the at least one electrolyte is adjusted without a transient or permanent net efflux of fluid from the patient's blood. In certain aspects the volume of the patient's blood in the extracorporeal circuit remains constant throughout the performance of the method. In other aspects the volume of the patient's blood in the extracorporeal circuit does not vary by more than 0.5, 1, 2, 3, 4, 5% throughout performance of the method. In a particular aspect the volume of the patient's blood in the extracorporeal circuit does not vary by more than 1% throughout performance of the method. In certain aspects the concentration of the at least one electrolyte is adjusted without addition of fluid to a patient's blood other than fluid that flows across the semipermeable barrier in the filter. In certain aspects the concentration of the at least one electrolyte is adjusted without withdrawing fluid from the patient's blood other than fluid that flows across the semipermeable barrier in the filter.

In certain aspects the second filter chamber is in fluid communication with a wash solution input pump controlling the rate of flow of wash solution into the second filter chamber and an effluent pump controlling the rate of flow of effluent out of the second filter chamber. The method can further comprise adjusting the rates of the wash solution input pump and the effluent pump to cause a lower pressure in the second filter chamber than the pressure in the first filter chamber and a net efflux of fluid from the patient's blood. The method can further comprise measuring the pressure in the second filter chamber. In certain aspects the pressure in the second filter chamber is 0 to −300 mmHg relative to the first filter chamber. The method can include adjusting the rate of the wash solution input pump and/or the effluent outlet pump based on the pressure measurement or pressure differential between the first filter chamber and the second filter chamber. In certain aspects the method includes adjusting the rate of the wash solution input pump and/or the effluent pump comprises stopping the wash solution input pump and/or the effluent pump if the pressure in the second filter chamber is higher than the pressure in the first filter chamber. In certain aspects the second filter chamber can be in fluid communication with a plurality of wash solutions, 2, 3, 4, 5, 6, 7, 8, 9, 10 or more wash solutions, including all values and ranges there between.

In certain aspects the wash solution input pump and the effluent outlet pump are electrically coupled to (i) a sensor that senses the concentration of the at least one electrolyte in the patient's blood and (ii) a processor that receives electrolyte concentration data from the sensor and controls the rate of flow of wash solution through the second filter chamber by adjusting the rates of the wash solution input pump and the effluent pump based on the electrolyte concentration data.

Certain embodiments are directed to methods of preparing stored blood for injection into a patient comprising. The methods can include (a) providing a filter in fluid communication with a reservoir containing the stored blood, wherein the filter comprises a first filter chamber and a second filter chamber separated by a semipermeable barrier; (b) flowing the stored blood through the first filter chamber; (c) adjusting the concentration of at least one electrolyte in the stored banked blood by flowing a wash solution through the second filter chamber in a direction of flow opposite to the direction that the patient's blood is flowing through the first filter chamber.

Certain embodiments are directed to a system for adjusting the concentration of at least one electrolyte in a patient's blood. The system can include (a) blood flow tubing in fluid communication with the patient's circulatory system; (b) an oxygenator in fluid communication with the blood flow tubing; (c) a blood pump that causes blood to flow within the blood flow tubing; (d) a filter comprising a first filter chamber and a second filter chamber separated by a semipermeable barrier, wherein the first filter chamber is in fluid communication with the blood flow tubing; (e) a wash solution reservoir in fluid communication with the second filter chamber; and (f) a wash solution input pump in fluid communication with the wash solution reservoir that causes the wash solution to flow within the second filter chamber in a direction opposite the direction of blood flow. In certain aspects the wash solution input pump is upstream from and in fluid communication with a wash solution inlet port, the wash solution inlet port being in fluid communication with the second filter chamber. The system can further include an effluent pump downstream from and in fluid communication with an effluent outlet port, the effluent outlet port being in fluid communication with the second filter chamber. In certain aspects the system includes a pump speed controller that can adjust the speed of the wash solution input pump and/or the effluent pump. The system can also include a display that indicates the rate of the wash solution input pump and/or the effluent pump. In certain aspects the wash solution input pump, the effluent pump, the pump speed controller, and the display are comprised in a single, portable console. The system can also include a sensor that can detect the concentration of at least one electrolyte in the patient's blood. The sensor can be configured to communicate electrolyte concentration data to a processor. The processor can cause a change in speed of the wash solution input pump and/or the effluent pump based on the electrolyte concentration data. The system can also include a pressure sensor in fluid communication with the second filter chamber. A safety shut-off mechanism can be included that can stop the wash solution pump and/or the effluent pump if the pressure in the second filter chamber is outside a predetermined range. The wash solution reservoir can contain a wash solution having 133-145 mmol/L sodium, a pH of 7.35-7.45, 22-28 mmol/L bicarbonate, 95-115 mmol/L chloride.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa.

The term "crystalloid" refers to small molecules (usually less than 10 Å) such as salts, sugars, and buffers.

The use of the word "a" or "an" when used in conjunction with the term "comprising" in the claims and/or the specification may mean "one," but it is also consistent with the meaning of "one or more," "at least one," and "one or more than one."

The term "about" or "approximately" are defined as being close to as understood by one of ordinary skill in the art. In one non-limiting embodiment the terms are defined to be within 10%, preferably within 5%, more preferably within 1%, and most preferably within 0.5%.

The term "substantially" and its variations are defined to include ranges within 10%, within 5%, within 1%, or within 0.5%.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods of making and using the same of the present invention can "comprise," "consist essentially of," or "consist of" particular ingredients, components, blends, method steps, etc., disclosed throughout the specification.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DETAILED DESCRIPTION OF THE INVENTION

The device, system, and methods described herein can be used to maintain the physiologic state of a patient through the entire electrolyte spectrum. It began with the quest to create a crystalloid solution that would maintain the appropriate electrolyte ranges while lowering targeted values. A custom pH balanced perfusion specific crystalloid solution had been used in the past. This simple crystalloid solution was beneficial but another problem that was not solved by the customized crystalloid solution was the unmet need for removing fluid quickly via a hemofilter. As mentioned before, the electrolytes are a major focus during the surgeries, but one of the most important factors that is directly affected while the blood is "washed" is the hematocrit. As volume is added to the patient to dilute the electrolytes it also dilutes the total red cell volume. Acute changes like this can affect the oxygen carrying capacity of the patient, the vascular tone, and can impact end organ perfusion. Hemofiltration is a great tool but very slow relative to a rapid paced cardiac surgery. The limitation is that one cannot add a large bolus of fluid to a patient repeatedly because of its negative affects so the fluid must be parceled and removed, add fluid then remove fluid and add fluid then remove fluid. This is where the term "washing" the blood originates. The problem is that the excessive amount of volume takes a certain amount of time to remove before the process can continue. The inventors contemplated modifying or manipulating the hemofilter to increase its efficiency when used in conjunction with customized physiologic crystalloid solutions.

The theory of infusing by electrolyte counter current to the blood being shunted through the hemofilter would cause a diffusion of the electrolytes without the need of adding the volume into the patient's blood stream. As the blood passes through the hemofilter fibers and the optimized electrolyte solution moves around those fibers the electrolytes seek an equilibrium from the electrolyte gradient between the patient's blood going through the inside of the fibers of the hemofilter versus the electrolytes in the custom crystalloid flowing counter current on the outside of the fibers.

The device described herein is a small, light-weight, self-contained system that can be adapted to any cardiopulmonary bypass Heart/Lung machine, extracorporeal membrane oxygenation console, or stand-alone unit for restoration of undesirable banked blood.

A. Extracorporeal Conditioning System

Device described herein can be operated in 1, 2, 3, 4 or more different modes: (1) "zero balanced" electrolyte transfer, (2) fluid removal, (3) a combination of both electrolyte transfer and fluid removal simultaneously, and (4) physiological restoration of banked blood. Buttons can be present to select modes or dictate pump speeds during the combo mode. This system can provide a more precise and efficient level of ultrafiltration, thus allowing the patient to maintain an optimum pH and electrolyte balance during heart surgery, during application of ventricular assist devices (VAD's), as well as during extracorporeal membrane oxygenation (ECMO) runs.

Figure 1:
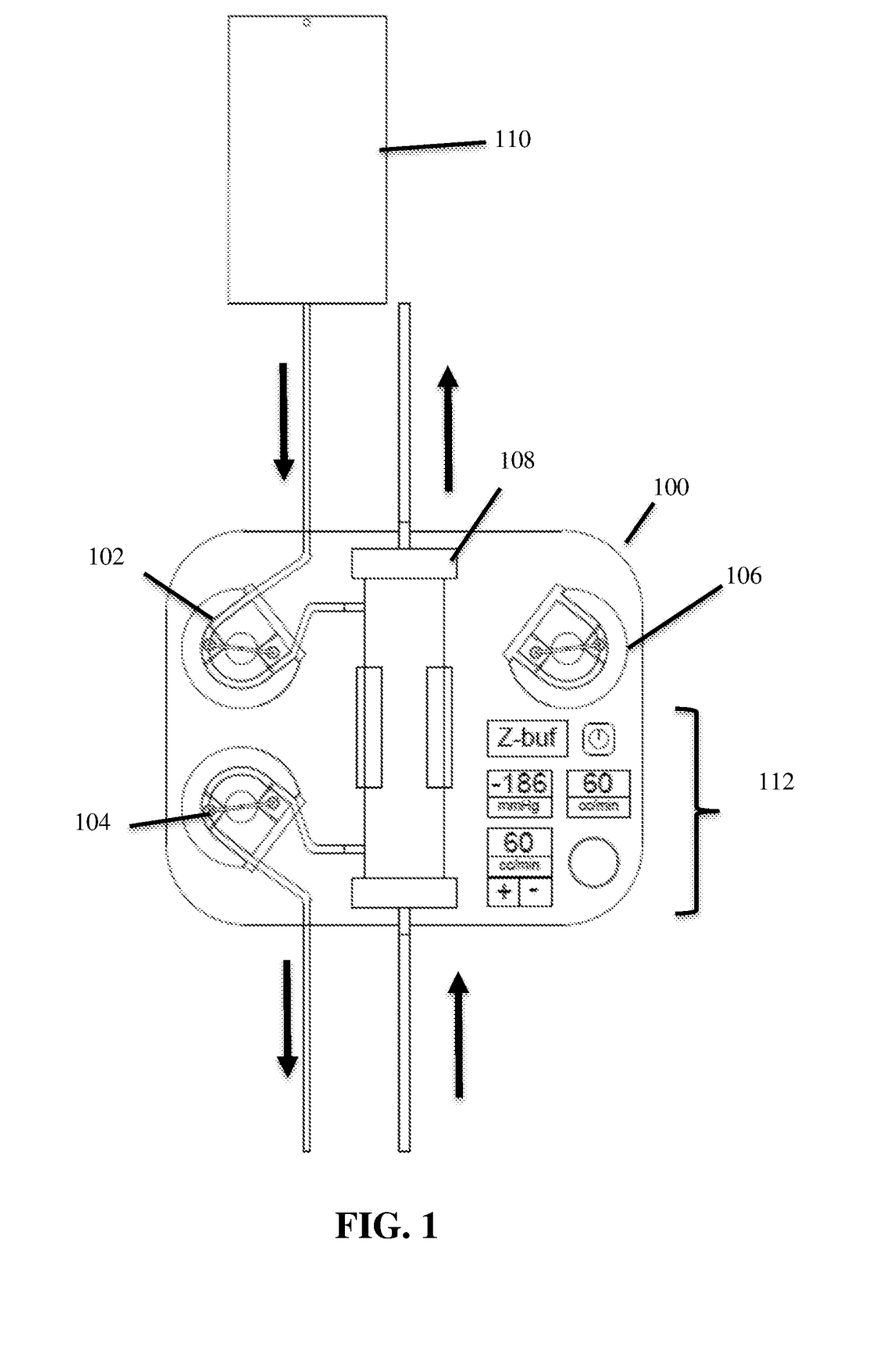
FIG. 1. This drawing illustrates one embodiment of a device as described herein.

Referring to FIG. 1, the system is comprised of console 100 with dual roller pumps 102 and 104 to be used in conjunction with preassembled sterile disposable, hemofilter 108 as well as an optimum pH and electrolyte balanced cardiovascular solution 110. Multiple displays 112 on the console show each pumps flow rate (ml/min) and the pressure (mmHg) on the negative side of the outlet pump.

Hemofilters are used in many cardiovascular cases. Blood is usually shunted through the hemofilter which contains hundreds of semipermeable microporous fibers and then reenters the patients cardiopulmonary support circuit. The pores are small enough to allow only small molecules, like aqueous solutions, electrolytes or anything else that is smaller than 50,000 Daltons. If molecules are greater than 50,000, like plasma proteins, blood cells, and most other blood components, they will not pass through the pores and will remain in the circuit and patient circulation. As a negative pressure is applied to the hemofilter, the aqueous fluid is removed which essentially concentrates the contents of the blood.

Continuing reference to FIG. 1, the two roller pumps (e.g., 102 and 104 of FIG. 1), designated as the inlet (102) and outlet (104) pumps can perform synchronously or independently from each other. For different situations different modes have been incorporated, for example Z-buf (1), Concentration (2), Combo (3) and Restoration (4). The different modes can be utilized during the following examples. (i) During heart surgery, it is not uncommon for the patient's pH and electrolytes to become out of balance due to multiple outside factors such as normal saline (pH 5.0) injection from the surgical table or doses of high potassium cardioplegia solution (K>7). Traditional treatment of these issues would be the administration of sodium bicarbonate for pH correction and the addition of 0.9% NaCl to the patient's bypass circuit to reduce an elevated potassium level by diluting it. The diluted volume is then removed via ultrafiltration. This method is time consuming and inefficient and other electrolytes could subsequently become imbalanced such as chloride. With the device/system described herein the top pump or inlet pump 102 pulls the sterile pH/electrolyte balanced cardiovascular solution from bag 110 and pumps it into hemofilter 108. This solution moves counter current outside of the fibers, as the blood pathway moves inside the hemofilter fibers. Outlet pump 104 draws fluid from within the hemofilter and can expel it to a proper waste container. With safety in mind, a pressure monitor is attached on the negative side of outlet pump 104 from hemofilter 108, in order to assure that a negative pressure is maintained. Safe guards can be provided or built in to stop both the pumps if the pressure becomes positive or if it becomes too negative. Another safety feature that can be incorporated is that the inlet pump that pushes fluid into the hemofilter can be regulated to never to run at a higher flow rate than the outlet pump which pulls fluid from the system. As the pH/electrolyte balanced cardiovascular solution runs through the hemofilter, the electrolytes within the blood shift to establish an equilibrium between the solution and the blood. If undesirable or even dangerous electrolyte levels are present this device can be employed to rapidly, yet safely, reduce and balance the pH and electrolyte levels to their normal physiological state in a very short amount of time. When inlet 102 and outlet 104 pumps move at the same speed there is a net zero balance of fluid between the patient and the electrolyte transfer system.

In the event that only fluid removal is necessary from the patient bypass circuit, the system has a mode that will remove fluid more efficiently than the traditional ultrafiltration method of vacuum only. This mode will require that the inlet pump does not rotate and the outlet pump responds to the users designated removal rate. Also, included in this system is a mode which is a combination of the counter current technique with additional fluid removal. This combo mode can be used in the event that the patient's electrolytes require to be normalized, but fluid also needs to be removed. For example electrolyte imbalances can occur when the hematocrit needs to be elevated. This can occur because even "fresh" packed red blood cells typically have an elevated potassium and pH imbalance. With the combo mode engaged one can increase the hematocrit and restore the optimum physiologic state of the blood in a matter of minutes.

In certain embodiments the console is electrically powered, small, light-weight and water resistant. A bracket can be provided, preferably on the back side, so the console can easily be attached to any brand of cardiopulmonary bypass machines or ECMO consoles. The accompanying sterile disposable can come fully assembled and easily pops onto the device.

Figure 2:
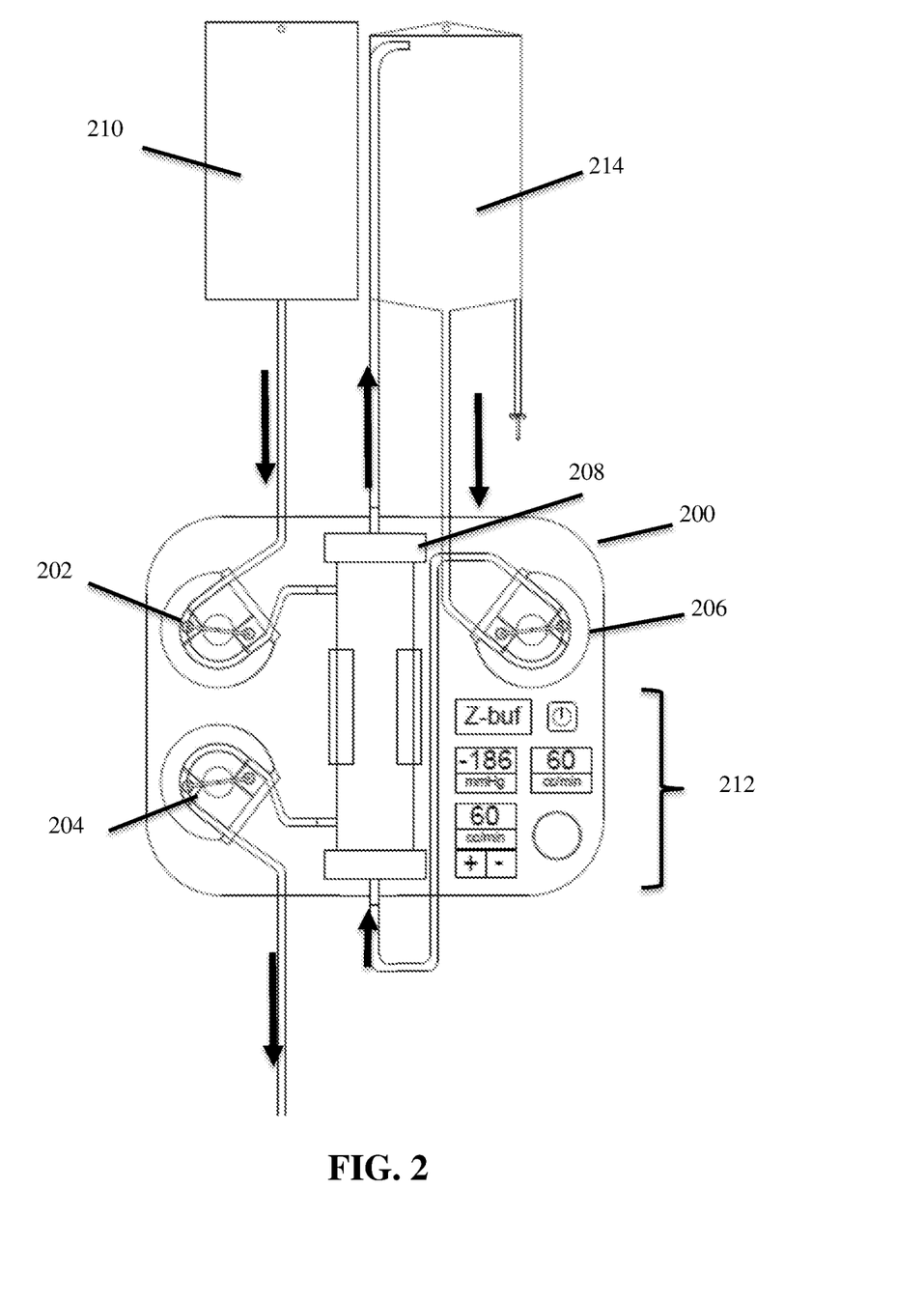
FIG. 2. This drawing illustrates a second embodiment of a device as described herein, this device is configured for blood restoration.

The sterile disposable can be used as an additional component to a cardiovascular bypass system, the primary use. The device has a secondary use which can be implemented as a stand-alone unit. With reference to FIG. 2, the sterile disposable is functionally different and can be used for the restoration of banked blood. The two different systems can employ custom pH/electrolyte balanced cardiovascular solutions. For the primary use the pH/electrolyte balanced cardiovascular solution can be broken down into two types. Solution A will be composed of a physiologic pH balanced crystalloid that includes sodium, calcium, chloride and glucose within their normal ranges. Solution B will contain the same components but will also incorporate potassium in a normal physiologic range. The secondary use disposable will also include a pH balance crystalloid solution similar to solution B but it will not contain calcium. The calcium will interfere with the anticoagulant, citrate, of the banked blood causing it to clot.

The system illustrated in FIG. 2 includes console 200 having inlet pump 202, outlet pump 204 in communication with solution bag 210 and hemofilter 208. Console 200 has display 212. The device is also configured to be in communication with blood source 214 which is in communication with hemofilter 208. The blood is counter flow circulated relative to the solution provided by solution bag 210 by pump 206.

B. Methods of Regulating Electrolyte Levels

The devices, systems, and methods described herein could be used safely on any cardiopulmonary bypass circuit, ECMO, or temporary ventricular assist device. This device could be used to normalize a cardiopulmonary circuit before it is used on a patient. As a unit of blood ages, the cell wall of the red blood cell begins to deteriorate and can eventually rupture. The patient will be exposed to the noxious contents of the ruptured cell if they are transfused with this blood. The secondary use of the device/system will help normalize the electrolytes, primarily potassium and glucose of banked blood. The speed, efficiency, and portability of the device in tandem with the custom crystalloid solutions, and sterile disposables make it a unique system that can be utilized in various hospital settings.

The traditional method for fluid removal has been to simply remove fluid with a hemofilter from the cardiopulmonary bypass circuit. The device/system described herein allows for fluid removal as well as a counter current fluid transfer to quickly manipulate the patient's electrolytes or return banked blood to a physiologic state. The pH/electrolyte balanced solutions in conjunction with the counter current flow is distinct from the current industry wide practice.

With the proper pH/electrolyte balanced cardiovascular solution the inventors have shown proof of concept. The unexpected results encountered was extreme efficiency of the system.

EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Maintaining Physiological Status while on Cardiopulmonary Bypass Utilizing Electrolyte Transfer and Custom Perfusion pH Balanced Solutions A representative system was tested on a circuit of expired blood with adverse pH/electrolyte levels. The device was used with a pH/electrolyte balanced cardiovascular solution and the pH/electrolyte levels were normalized within minutes of starting the mechanism. In one experiment the potassium was lowered from 8.7 to 3.9 in approximately 6 minutes. This is a significant achievement when compared to the traditional method.

A. Materials and Methods

Studies were performed to recreate a clinical setting and compare an embodiment of the current invention to traditional methodologies. The improved counter current system described herein and custom pH balanced crystalloid solution is compared to the industry wide practice of the use of traditional crystalloids with traditional hemofiltration, which would serve as the control group. After a cardiac surgery takes places there is occasionally a portion of the patient's blood left in the cardiopulmonary bypass machine that will be discarded once the patient's surgery is complete and the patient has left the operating room. Studies utilized this discarded human blood. The electrolyte levels are manipulated to mimic the undesirable levels one may experience on bypass. Once the mimic conditions were established the inventors would attempt to compare the two techniques. Also, the blood bank at times has expired blood and fresh frozen plasma, which can be used to prime the circuits to simulate situations of undesirable levels of the electrolytes while on cardiopulmonary bypass.

One disclaimer is that the inventors chose to use their own wash solution noted as "Wash A" because it is the inventor's clinical experience that this is an optimal crystalloid when compared to normal saline. Wash A has a sodium level of 138 mmol/L and balance pH, where 0.9% NaCl has a sodium of 154 and a pH of 5.0. Over a 12 minute span 305 mL of packed red blood cells were given to increase the hematocrit and 600 mL of Wash A was added to lower the potassium level. A reminder is that this large amount of volume added to a circuit takes a certain amount of time to reach its original volume when using a hemoconcentrator. In this 12 minutes a 14% drop in the potassium was experienced, the wash was continued for an additional 18 minutes with 600 mL added and 57% drop was recorded. At this point the inventors were 30 minutes into the traditional method with 1200 mL of wash used. It is noteworthy to observe the other electrolytes during this process and their changes. Sodium bicarbonate and calcium were added and then an additional 13 minutes of Wash B was used. Wash B is similar to Wash A, but it contains a physiologic level of potassium. The end result was a circuit blood gas that resembled the patient's baseline, the problem is that it took 51 minutes and 1500 mL of washing to achieve this.

B. Results

In the traditional method, table 1, an actual patient baseline gas is provided in column 1, the first gas evaluated on the circuit is in column 2. It is noted that the potassium has been artificially elevated. One disclaimer is that the inventors chose to use their own wash solution noted as "Wash A" because it is the inventor's clinical experience that this is an optimal crystalloid when compared to normal saline. Wash A has a sodium level of 138 mmol/L and balance pH, where 0.9% NaCl has a sodium of 154 and a pH of 5.0. Over a 12 minute span 305 mL of packed red blood cells were given to increase the hematocrit and 600 mL of Wash A was added to lower the potassium level. A reminder is that this large amount of volume added to a circuit takes a certain amount of time to reach its original volume when using a hemoconcentrator. In this 12 minutes a 14% drop in the potassium was experienced, the wash was continued for an additional 18 minutes with 600 mL added and 57% drop was recorded. At this point the inventors were 30 minutes into the traditional method with 1200 mL of wash used. It is noteworthy to observe the other electrolytes during this process and their changes. Sodium bicarbonate and calcium were added and then an additional 13 minutes of Wash B was used. Wash B is similar to Wash A, but it contains a physiologic level of potassium. The end result was a circuit blood gas that resembled the patient's baseline, the problem is that it took 51 minutes and 1500 mL of washing to achieve this.

TABLE 1

| Traditional Method | Patient Gas | Circuit | 12 minutes 305 mL PRBC and 600 mL Wash A Added | 18 minutes 600 mL Wash A | 8 minutes Added 6 mEq NaHCO$_3$ and 250 mg CaCl | 13 minutes Sweep Adjustment and 300 mL Wash B |
|---|---|---|---|---|---|---|
| pH | 7.42 | 7.18 | 7.19 | 7.35 | 7.48 | 7.41 |
| Sodium (mmol/L) | 137 | 137 | 138 | 137 | 144 | 142 |
| Potassium (mmol/L) | 3.9 | 11.4 | 9.8 | 4.2 | 3.9 | 3.8 |
| Calcium (mmol/L) | 1.21 | 1.25 | 0.63 | 0.42 | 1.91 | 1.05 |
| Chloride (mmol/L) | 108 | 106 | 109 | 111 | 116 | 105 |
| Glucose (mg/dL) | 116 | 313 | 249 | 128 | 119 | 66 |
| Base Excess (mmol/L) | −3.1 | −12 | −13.8 | −5.2 | 3.9 | 1.2 |
| Bicarb (mmol/L) | 20.8 | 15.3 | 13.4 | 19.9 | 27.6 | 26 |
| Hematocrit (%) | 29 | 17 | 32 | 27 | 29 | 29 |
| Lactate | 1.0 | 8.0 | 7.9 | 4.6 | 4.7 | 3.0 |

51 minutes and 1500 mL of Wash A added

In the rapid electrolyte transfer experiment (table 2) the countercurrent system was set up on the circuit and no fluid was added into the mock patient's circulation. The efficiency of the system was immediately apparent. Wash A was used and within 3 minutes the inventors had achieved a 26% decrease in the potassium level while maintaining the pH and hematocrit. The process was continued for 3 additional minutes and an additional 39% decrease in the potassium was achieved which ultimately restored it to a physiologic level. In this experiment the glucose and lactate were reduced yet the pH, sodium and hematocrit were maintained. An overall 55% reduction is potassium was accomplished in 6 minutes.

TABLE 2

Rapid ETS method

| Rapid ETS Method | Simulated circuit Gas | 3 Minutes 300 mL of Wash A | 3 Minutes 300 mL Wash A |
|---|---|---|---|
| pH | 7.33 | 7.35 | 7.38 |
| Sodium (mmol/L) | 130 | 134 | 137 |
| Potassium (mmol/L) | 8.7 | 6.4 | 3.9 |
| Calcium (mmol/L) | 1.05 | 0.9 | 0.69 |
| Chloride (mmol/L) | 100 | 101 | 102 |
| Glucose (mg/dL) | 249 | 208 | 153 |
| Base Excess (mmol/L) | −3.1 | −1.4 | 0.6 |
| Bicarb (mmol/L) | 22.7 | 24.3 | 26 |
| Hematocrit (%) | 30 | 31 | 31 |
| Lactate | 2.3 | 2.0 | 1.5 |

6 minutes and 600 mL of zero balance

An additional method was conceived that could use a slow and continuous method to maintain the physiology versus making quick drops in the potassium. Wash A and B were both used in a countercurrent method. The countercurrent system was run at a much slower pace to measure its effects. 60 mL was used every 3 minutes versus the 300 mL in the previous electrolyte transfer experiment and the results were still favorable. The initial 3 minutes saw a 22% drop in potassium, then 12% on the next 3, 16% and then 11.6%. This brought potassium to a normal range and wash B was used.

The results were promising. Never before have the inventors been able to influence targeted electrolytes without significantly impacting others. It's almost as though one problem is fixed while another problem is created. The speed and efficiency is something that was unexpected when the experiment was initiated. Based on these results an electrolyte transfer system used in conjunction with an optimized perfusion specific crystalloid solution is much better than the industry wide standard.

TABLE 3

Continuous ETS Method

| Continuous ETS Method | Simulated Patient Gas | 3 minutes 60 mL WashA | 3 minutes 60 mL WashA | 3 minutes 60 mL WashA | 3 minutes 60 mL WashB | 3 minutes 60 mL WashB | 2 minutes 40 mL WashB |
|---|---|---|---|---|---|---|---|
| pH | 7.49 | 7.46 | 7.46 | 7.46 | 7.47 | 7.45 | 7.43 |
| Sodium (mmol/L) | 135 | 137 | 138 | 139 | 140 | 140 | 140 |
| Potassium (mmol/L) | 9.0 | 7.0 | 6.1 | 5.1 | 4.5 | 4.1 | 4.0 |
| Calcium (mmol/L) | 1.33 | 1.31 | 1.30 | 1.29 | 1.29 | 1.28 | 1.25 |
| Chloride (mmol/L) | 98 | 97 | 98 | 98 | 99 | 97 | 95 |
| Glucose (mg/dL) | 216 | 188 | 176 | 165 | 159 | 150 | 137 |
| Base Excess (mmol/L) | 7.2 | 4.9 | 4.9 | 4.9 | 5.6 | 4.1 | 2.6 |
| Bicarb (mmol/L) | 31.2 | 29.2 | 29.2 | 29.2 | 29.8 | 28.5 | 27.2 |
| Hematocrit (%) | 38 | 38 | 37 | 36 | 36 | 38 | 37 |
| Lactate | 3.9 | 3.3 | 3.1 | 2.8 | 2.7 | 2.5 | 2.2 |

20 minutes and 340 mL of zero balance

The invention claimed is:

1. A method of establishing physiological conditions in a patient's whole blood while the patient is connected to a cardiopulmonary bypass machine including a blood pump that produces a blood pressure of the patient's whole blood and the patient's whole blood to flow within the cardiopulmonary bypass machine to maintain the physiological conditions of the patient's circulation, the method comprising:
 (a) providing a self-contained system having a filter, wherein the filter comprises a first filter chamber and a second filter chamber separated by a semi-permeable barrier, the first filter chamber connected to blood flow inlet tubing and blood flow outlet tubing and the second filter chamber connected to wash solution inlet tubing and wash solution outlet tubing;
 (b) connecting the blood flow inlet tubing of the self-contained system to the cardiopulmonary bypass machine;
 (c) connecting the blood flow outlet tubing of the self-contained system to the cardiopulmonary bypass machine;
 (d) flowing the patient's whole blood through the first filter chamber and the blood flow inlet tubing under the blood pressure of the patient's whole blood created by the cardiopulmonary bypass machine, the first filter chamber being shunted under the blood pressure of the patient's blood from the cardiopulmonary bypass machine, the patient's whole blood flowing in a first direction through the first filter chamber, through the blood flow outlet tubing and into the cardiopulmonary bypass machine;

(e) flowing a first wash solution through the second filter chamber and wash solution inlet and outlet tubing in a second direction of flow, the first direction being generally opposite the second direction, a wash solution input pump controlling a rate of flow of the first wash solution into the second filter chamber and an effluent pump controlling a rate of flow of effluent out of the second filter chamber;

(f) controlling the rate of flow of the first wash solution and the rate of flow of the effluent based on a pressure in the second filter chamber; and (g) normalizing a cardiopulmonary circuit of the cardiopulmonary bypass machine before connecting the cardiopulmonary bypass machine to the patient and prior to step (d) by normalizing electrolytes in blood in the cardiopulmonary bypass machine.

2. The method of claim 1, wherein an electrolyte in the patient's whole blood comprises at least one of a hydrogen ion, sodium, potassium, calcium, chloride, glucose, bicarbonate, and lactate.

3. The method of claim 2, wherein step (c) is performed for a time sufficient to cause a concentration of the electrolyte in the patient's whole blood to adjust from outside of a physiological range to within the physiological range.

4. The method of claim 3, wherein performing step (c) causes the concentration of the electrolyte in the patient's whole blood to adjust to the concentration within the physiological range within 6 minutes of initiating flow of the first wash solution through the second filter chamber.

5. The method of claim 4, wherein performing step (c) causes the concentration of the electrolyte in the patient's blood to adjust by at least 15% within 3 minutes.

6. The method of claim 1, wherein the first wash solution comprises an electrolyte at an electrolyte concentration below an electrolyte concentration in the patient's whole blood before step (c) is performed.

7. The method of claim 1, wherein the first wash solution comprises an electrolyte at an electrolyte concentration above an electrolyte concentration of the patient's blood before step (c) is performed.

8. The method of claim 1, wherein a total volume of the first wash solution that is flowed through the second filter chamber in step (c) is less than 600 ml, wherein a rate of flow of the first wash solution through the second filter chamber is from 20 to 200 ml/min and wherein a rate of flow of the patient's whole blood through the first filter chamber is from 20 to 200 ml/min.

9. The method of claim 1, further comprising:
flowing a second wash solution through the second filter chamber after a concentration of an electrolyte in the patient's whole blood is adjusted to be within a physiological range, wherein the second wash solution has an electrolyte concentration within the physiological range.

10. The method of claim 1, wherein a concentration of sodium in the patient's whole blood remains below 140 mM or does not increase by more than 5% while the method is being performed and wherein performing the method does not cause a decrease in a hematocrit of the patient's whole blood of more than 3%.

11. The method of claim 1, wherein a concentration of an electrolyte in the patient's whole blood is adjusted without adding fluid to a reservoir of the patient's whole blood in the cardiopulmonary bypass machine and without a transient or permanent net influx of fluid into the patient's whole blood.

12. The method of claim 1, wherein a concentration of an electrolyte in the patient's whole blood is adjusted without addition of fluid to the patient's whole blood other than fluid that flows across the semi-permeable barrier in the filter and without withdrawing fluid from the patient's whole blood other than fluid that flows across the semi-permeable barrier in the filter.

13. The method of claim 1, further comprising:
adjusting the rates of flow of the first wash solution and the effluent to cause a lower pressure in the second filter chamber than the blood pressure in the first filter chamber, the lower pressure in the second filter chamber producing a net efflux of fluid from the patient's whole blood.

14. The method of claim 1, further comprising:
measuring a pressure in the second filter chamber and adjusting the rate of flow of the first wash solution and/or the rate of flow of effluent based on the pressure in the second filter chamber.

15. The method of claim 13, wherein the wash solution input pump and the effluent pump are electrically coupled to (i) a sensor that senses a concentration of an electrolyte in the patient's blood and (ii) a processor that receives electrolyte concentration data from the sensor and controls the rate of flow of the first wash solution through the second filter chamber by adjusting the wash solution input pump and the effluent pump based on the electrolyte concentration data.

16. The method of claim 1, further comprising:
decreasing a volume of the patient's whole blood while simultaneously adjusting a concentration of an electrolyte in the patient's whole blood to physiological levels and maintaining the concentration of the electrolyte in the patient's blood at the physiological levels.

17. The method of claim 1, further comprising:
controlling the wash solution input pump and the effluent pump in a zero balanced electrolyte transfer mode.

18. The method of claim 1, further comprising:
controlling the wash solution input pump and the effluent pump in a fluid removal mode, wherein the wash solution input pump does not rotate and the effluent pump operates at a user designated removal rate.

19. The method of claim 1, further comprising:
controlling the wash solution input pump and the effluent pump in a combination mode, wherein electrolytes are transferred from the first wash solution to the patient's whole blood and fluid is removed from the patient's whole blood.

20. The method of claim 1, wherein the effluent flows to waste from wash solution outlet tubing on a downstream side of the effluent pump.

21. The method of claim 1, further comprising:
(h) receiving a pressure in the second filter chamber from a pressure sensor in fluid communication with the second filter chamber at a pump speed controller.

22. The method of claim 21, wherein the pump speed controller sends signals to the wash solution input pump and the effluent pump to control the rate of flow of the first wash solution and the rate of flow of the effluent based on the pressure in the second filter chamber.

23. The method of claim 1, wherein the cardiopulmonary bypass machine is comprised of a first cardiopulmonary bypass machine, the filter is comprised of a first disposable filter, the method comprising:
(h) disconnecting the blood flow inlet tubing and the blood flow outlet tubing from the first cardiopulmonary bypass machine;
(i) removing and disposing the first disposable filter;

(j) connecting the second filter chamber to the self-contained system, the second filter chamber having second blood flow inlet tubing and second blood flow outlet tubing;

(k) connecting the second blood flow inlet tubing to a second cardiopulmonary bypass machine; and (l) connecting the second blood flow outlet tubing to the second cardiopulmonary bypass machine.

24. The method of claim 23, wherein the first cardiopulmonary bypass machine is comprised of a first cardiopulmonary heart/lung machine and the second cardiopulmonary bypass machine is comprised of a second cardiopulmonary heart/lung machine.

25. The method of claim 1, further comprising:

(h) flowing the patient's whole blood from the first filter chamber through the blood flow outlet tubing and back into the cardiopulmonary bypass machine.

26. A method of establishing physiological conditions in a patient's blood while the patient is connected to a cardiopulmonary bypass machine, including a cardiopulmonary bypass heart/lung machine, that produces a blood pressure of the patient's blood, the method comprising:

(a) providing a self-contained system having a filter configured for connection to the cardiopulmonary bypass machine and a controller, the filter includes a first filter chamber and a second filter chamber separated by a semi-permeable barrier, the first filter chamber connected to blood flow inlet tubing and blood flow outlet tubing and the second filter chamber connected to wash solution inlet tubing and wash solution outlet tubing;

(b) connecting the blood flow inlet tubing to the cardiopulmonary bypass machine at a medical facility;

(c) connecting the blood flow outlet tubing to the cardiopulmonary bypass machine at the medical facility;

(d) flowing the patient's blood through the first filter chamber and the blood flow inlet and outlet tubing, the patient's blood flowing in a first direction through the first filter chamber;

(e) flowing a first wash solution through the second filter chamber and wash solution inlet and outlet tubing in a second direction of flow, the first direction being generally opposite the second direction, a wash solution input pump controlling a rate of flow of the first wash solution into the second filter chamber and an effluent pump controlling a rate of flow of effluent out of the second filter chamber;

(f) controlling the rate of flow of the first wash solution and the rate of flow of the effluent based on a pressure in the second filter chamber;

(g) normalizing a cardiopulmonary circuit of the cardiopulmonary bypass machine before connecting the cardiopulmonary bypass machine to the patient and prior to step (d) by normalizing electrolytes in blood in the cardiopulmonary bypass machine;

(h) operating the self-contained system with the controller in the following modes:

(i) an electrolyte transfer mode configured to maintain a blood volume of the patient while adjusting a concentration of an electrolyte in the patient's blood;

(ii) a fluid removal mode configured to decrease a total volume of the patient's blood; and (iii) a combination mode configured to decrease the total volume of the patient's blood while simultaneously one of adjusting the concentration of the electrolyte in the patient's blood to physiological levels and maintaining the concentration of the electrolyte in the patient's blood at physiological levels.

27. The method of claim 26, wherein the cardiopulmonary bypass machine is comprised of a first cardiopulmonary bypass machine, the method comprising:

(i) disconnecting the blood flow inlet tubing and the blood flow outlet tubing from the first cardiopulmonary bypass machine;

(j) connecting the blood flow inlet tubing to a second cardiopulmonary bypass machine; and (k) connecting the blood flow outlet tubing to the second cardiopulmonary bypass machine.

28. The method of claim 26, wherein the medical facility is comprised of one of an operating room, an intensive care unit and an emergency room.

29. The method of claim 26, further comprising:

(i) stopping flow of the first wash solution through the second filter chamber when a concentration of a target electrolyte in the patient's blood is within a desired range; and (j) flowing a second wash solution through the second filter chamber.

30. The method of claim 26, further comprising:

(i) shutting off one of the wash solution input pump and the effluent pump when a pressure in the second filter chamber is outside a predetermined range.

31. The method of claim 26, wherein the self-contained system includes buttons to select the modes and dictate speeds of the wash solution input pump and the effluent pump of step (h).

32. The method of claim 26, wherein the controller controls the wash solution input pump and the effluent pump one of synchronously and independently in the modes.

* * * * *